United States Patent
Osborne et al.

(10) Patent No.: US 7,524,332 B2
(45) Date of Patent: Apr. 28, 2009

(54) VASCULAR VALVE WITH REMOVABLE SUPPORT COMPONENT

(75) Inventors: Thomas A. Osborne, Bloomington, IN (US); Brian C. Case, Bloomington, IN (US); David R. Lessard, Bloomington, IN (US); Neal E. Fearnot, West Lafayette, IN (US)

(73) Assignee: Cook Incorporated, Bloomington, IN (US)

( * ) Notice: Subject to any disclaimer, the term of this patent is extended or adjusted under 35 U.S.C. 154(b) by 399 days.

(21) Appl. No.: 10/549,437

(22) PCT Filed: Mar. 17, 2004

(86) PCT No.: PCT/US2004/008176

§ 371 (c)(1),
(2), (4) Date: May 2, 2006

(87) PCT Pub. No.: WO2004/082528

PCT Pub. Date: Sep. 30, 2004

(65) Prior Publication Data

US 2006/0212110 A1 Sep. 21, 2006

Related U.S. Application Data

(60) Provisional application No. 60/455,241, filed on Mar. 17, 2003, provisional application No. 60/491,490, filed on Jul. 31, 2003.

(51) Int. Cl.
A61F 2/24 (2006.01)
(52) U.S. Cl. ..................................... 623/2.14
(58) Field of Classification Search ........ 623/1.24–2.19

See application file for complete search history.

(56) References Cited

U.S. PATENT DOCUMENTS

| 4,218,782 A | 8/1980 | Rygg |
| 4,902,508 A | 2/1990 | Badylak et al. |
| 5,156,620 A | 10/1992 | Pigott |
| 5,411,552 A | 5/1995 | Andersen et al. |
| 5,554,389 A | 9/1996 | Badylak et al. |
| 5,607,465 A | 3/1997 | Camilli |
| 5,810,708 A * | 9/1998 | Woodard et al. .............. 600/16 |
| 5,855,601 A | 1/1999 | Bessler et al. |
| 5,993,844 A | 11/1999 | Abraham et al. |
| 6,099,567 A | 8/2000 | Badylak et al. |
| 6,110,201 A | 8/2000 | Quijano et al. |
| 6,126,686 A | 10/2000 | Badylak et al. |
| 6,168,614 B1 | 1/2001 | Andersen et al. |
| 6,200,336 B1 | 3/2001 | Badylak et al. |
| 6,206,931 B1 | 3/2001 | Cook et al. |
| 6,287,334 B1 | 9/2001 | Moll et al. |
| 6,299,637 B1 | 10/2001 | Shaolian et al. |

(Continued)

FOREIGN PATENT DOCUMENTS

EP 0856300 8/1998

(Continued)

*Primary Examiner*—Suzette J Gherbi
(74) *Attorney, Agent, or Firm*—Woodard, Emhardt, Moriarty, McNett & Henry LLP

(57) ABSTRACT

Described are vascular valve devices having valve elements formed of flexible material and at least one removable frame element. Also described are methods for using such devices in the vascular system and in particular in the venous system to treat venous insufficiency.

21 Claims, 12 Drawing Sheets

U.S. PATENT DOCUMENTS

| | | |
|---|---|---|
| 6,508,833 B2 | 1/2003 | Pavcnik et al. |
| 6,582,462 B1 | 6/2003 | Andersen et al. |
| 6,716,241 B2 | 4/2004 | Wilder et al. |
| 6,752,828 B2 | 6/2004 | Thornton |
| 6,936,067 B2 * | 8/2005 | Buchanan ............... 623/2.28 |
| 2001/0011187 A1 | 8/2001 | Pavcnik et al. |
| 2001/0039450 A1 | 11/2001 | Pavcnik et al. |
| 2002/0123800 A1 | 9/2002 | Taheri et al. |
| 2002/0188348 A1 | 12/2002 | DiMatteo et al. |
| 2003/0014126 A1 | 1/2003 | Patel et al. |
| 2003/0036795 A1 | 2/2003 | Andersen et al. |
| 2003/0130726 A1 | 7/2003 | Thorpe |
| 2003/0191525 A1 | 10/2003 | Thornton |
| 2003/0208261 A1 | 11/2003 | Thorpe et al. |
| 2003/0236568 A1 * | 12/2003 | Hojeibane et al. ........ 623/1.24 |
| 2004/0015230 A1 | 1/2004 | Moll et al. |
| 2004/0027557 A1 | 2/2004 | Caputo et al. |
| 2004/0049262 A1 | 3/2004 | Obermiller et al. |
| 2004/0193253 A1 | 9/2004 | Thorpe et al. |

FOREIGN PATENT DOCUMENTS

| | | |
|---|---|---|
| WO | WO 01/19285 | 3/2001 |
| WO | WO 03/002165 | 1/2003 |
| WO | WO 03/070124 | 8/2003 |

* cited by examiner

VASCULAR VALVE WITH REMOVABLE SUPPORT COMPONENT

REFERENCE TO RELATED APPLICATIONS

The present application is a national stage of International Patent Application PCT/US23004/008176 filed Mar. 17, 2004, which claims the benefit of U.S. Provisional Applications No. 60/455,241 filed Mar. 17, 2003 and No. 60/491,490 filed Jul. 31, 2003, all of which are hereby incorporated by reference.

BACKGROUND

The present invention resides generally in the field of medical devices, and more particularly relates to artificial valve devices such as those for implantation within the vascular system.

As further background, in all vertebrates, blood is transported away from the heart and throughout the body via arteries and returns to the heart through veins. To allow for optimal transport back to the heart and to reduce blood pressure build-up, veins contain various valves within their lumens, which open to permit blood flow to the heart but close to prevent the backflow of blood. Accordingly, venous valves function to provide the unidirectional flow of blood back to the heart.

Problems can arise when these venous valves fail to function properly. For example, venous valves can become incompetent or damaged by disease such that the backflow of blood is not prevented. When this occurs, blood pressure builds up and the veins and their valves become dilated, particularly in the lower extremities. If enough pressure builds up, the condition of venous insufficiency may develop. The severity of this condition is substantial, resulting in swelling, extensive pain, deformities, and, in the most severe cases, the development of ulcers can occur. If these ulcers become infected, amputation may ultimately be necessary to save the patient's life.

Currently, there is no proven cure for venous insufficiency. Basic treatments include elevation of the legs or the use of compression stockings. If surgery is determined to be necessary, vein stripping is typically performed, which involves the removal of the incompetent or damaged vein(s). Other surgical methods involve valvular reconstruction or transplantation.

Recently, the development of artificial and biological valves has been employed in an attempt to return normal pressure to the veins. There are a variety of these valves described in the art, which are generally designed to allow normal flow of blood back to the heart, while preventing retrograde flow. For example, U.S. Pat. No. 6,508,833 discloses a multiple-sided medical device comprising a closed frame of a single piece of wire or other resilient material and having a series of bends and interconnecting sides. The device has both a flat configuration and a second, folded configuration that comprises a self-expanding stent. The device is pushed from a delivery catheter into the lumen of a duct or vessel. A covering of fabric or other flexible material is sutured or attached to the frame to form an artificial valve. The flexible material utilized in the disclosed valves can be comprised of collagenous submucosa obtained from various animals, such as, for example, pigs, cattle, and sheep. This material can be processed and preserved so as to be capable of inducing host tissue proliferation, remodeling, and regeneration of appropriate tissue structures e.g., veins upon implantation in vivo (see, e.g., U.S. Pat. No. 6,485,723). The preparation of submucosal material is generally described in U.S. Pat. Nos. 4,902,508 and 5,554,389. The submucosal material can be prepared in large, flat sheets, which are subsequently cut and attached to a framing element, for example a stent, for deployment in a vein.

Despite work in the area there remain needs for medical products for grafting within the vasculature, including the venous system, to improve blood flow. The present invention addressed to these needs.

SUMMARY

In one embodiment, the invention provides a vascular valve device including an artificial valve for deployment within a vascular passage. The artificial valve includes flexible material and at least one frame element. The frame element is adapted for removal after deployment of the valve in the vessel, and the valve is configured to provide a valve function after removal of the frame element. Preferred devices include additional adaptations such as barbs, remodelable material, and multiple removable frame elements. Still further, the flexible material preferably comprises an extracellular matrix material, such as a submucosa.

In another embodiment, the invention provides a method for providing a valve in a vascular passage. An artificial valve is deployed in the passage, the valve including a flexible material and at least one frame element removable after deployment. The method includes a further step of removing the frame element so as to leave the artificial valve device within the vascular passage absent the frame element. The removal of the frame element can be performed before or after the artificial valve device has become attached to the vascular passage. Such attachment occurs when the edges of the valve have become attached to the walls of the vascular passage by endothelial or other tissue growth.

Another embodiment in the invention provides an artificial medical valve device that includes at least one leaflet formed with a flexible material. The leaflet has an edge for contacting a wall of a bodily passage upon deployment of the valve in the passage. Adaptations are provided along the edge for attaching the edge to the wall of the bodily passage. These adaptations may include, for example, barbs. At least one frame element is arranged along the edge of the leaflet and configured to force the edge against the passage wall for attachment upon deployment. The frame element is further removable after the deployment.

Additional embodiments as well as features and advantages of the invention will be apparent to those skilled in the art from the descriptions herein.

DETAILED DESCRIPTION OF THE PREFERRED EMBODIMENTS

Figure 1:
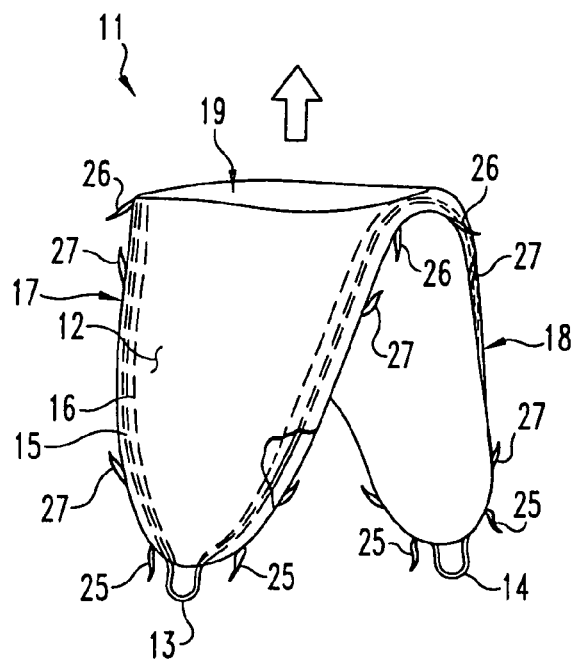
FIG. 1 provides a perspective view of a vascular valve device of the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated devices, and further applications of the principles of the invention as illustrated therein are herein contemplated as would normally occur to one skilled in the art to which the invention relates.

As disclosed above, in certain aspects, the present invention provides artificial valve devices such as heart valves or venous valves, and methods involving the use of the same. In certain aspects, the present invention provides medical valve devices including a flexible, leaflet-forming material, and at least one removable frame component. In other aspects, the present invention provides methods for implanting valve devices into a patient that involve delivering to a target site a valve device including a flexible, leaflet-forming material and at least one removable frame component, and removing the removable frame component.

Figure 2:
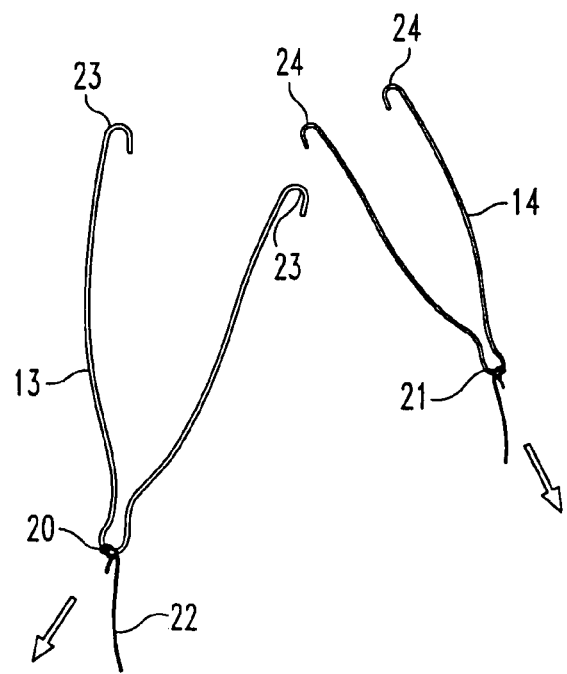
FIG. 2 provides a perspective view of the removable frame elements from the device of FIG. 1.

With reference now to FIGS. 1 through 3, illustrated is a first embodiment of the invention comprising a valve device 11 for deployment within the vascular system. Valve device 11 generally includes a flexible material 12, and removable frame elements 13 and 14. Frame elements 13 and 14 are received within sleeves 15 defined in the flexible material 12, for example, by stitches 16 positioned near the margin of the flexible material 12. Valve device 11 generally includes a first leg 17 and a second leg 18, each configured to support a leaflet upon deployment of the device 11 in a vascular passage. An opening 19 is defined in the flexible material 12 between legs 17 and 18, for allowing selective passage of blood through the device 11 in the direction of the arrow (FIG. 1).

Frame elements 13 and 14 include respective adaptations 20 and 21 for attachment of sutures 22 or similar devices effective for retrieval of the frame elements 13 and 14 after deployment of the device 11. In this regard, it will understood that alternatives to sutures 22 may include stylets, wires, or other elongate members effective for retrieval of the frame elements 13 and 14. Frame elements 13 and 14 also include generally curved portions 23 and 24 adapted to span between legs 17 and 18 of device 11 and provide effective resilient force to expand legs 17 and 18 such that they achieve contact with walls of the bodily passage in which device 11 is deployed.

Valve device 11 further includes barbs 25 located at a proximal end of device 11, and barbs 26 located at a distal end of device 11. Barbs 25 and 26 are directed generally back toward the deployment device and serve to resist movement of the device 11 during removal and retraction of frame elements 13 and 14. As well, barbs 25 and 26 resist movement of the device 11 upon the exertion of back-pressure by blood when the opening 19 is in its closed position. Device 11 may also include additional barbs 27 directed generally oppositely barbs 25 and 26, which can serve to resist movement of device 11 in the direction of blood flow (see arrow, FIG. 1). As incorporated in the illustrated device 11, the removable support component can be configured and arranged within the device to selectively force edges of the valve leaflets (and any associated attachment elements such as barbs) against the vessel wall. The barbs or other similar tissue-penetrating attachment elements can include attached eyelets, plates, or the like for attachment directly to the flexible material 12 such as by sewing. Alternatively or in addition, the barbs can be carried upon wires received and attached within sleeves 15 or otherwise to the flexible material 12, e.g. wherein the barb-carrying wires may remain implanted in the patient after removal of frame elements 13 and 14.

Figure 3A:
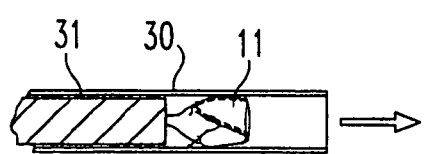
FIGS. 3A through 3C provide illustrations of a deployment of the valve device of FIG. 1.
Figure 3B:
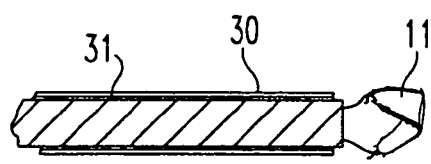
Figure 3C:
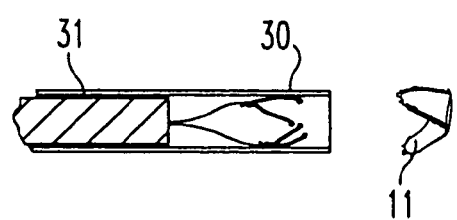
Figure 4:
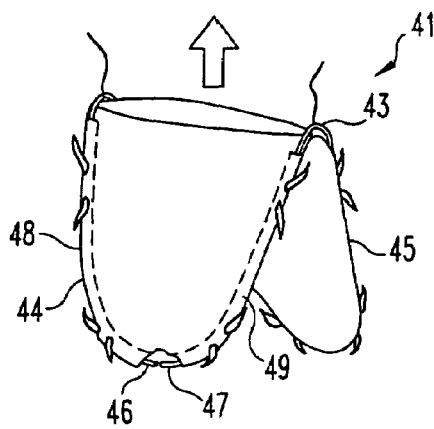
FIG. 4 provides a perspective view of an alternative valve device of the invention.

With reference now to FIGS. 3A through 3C, shown are steps in the deployment of device 11 from a delivery device 30 such as a catheter. Referring first to FIG. 3A, shown is device 11 received within a lumen of the catheter 30. Also provided is a push rod 31 which in the illustrated embodiment serves both to deploy device 11 and to retrieve the removable frame elements 13 and 14. Sutures 22 are attached both to frame elements 13 and 14 and to the end of push rod 31. With reference to FIGS. 3A and 3B together, push rod 31 is used to push device 11 in the direction of the arrow, and thereby deploy device 11 in a bodily passage in an expanded configuration. Shown in FIG. 3B is device 11 deployed, having frame members 13 and 14 remaining in device 11, and sutures 22 attached thereto. With reference now to FIG. 3C, when push rod 31 is retracted back into catheter 30, frame elements 13 and 14 are retrieved back into catheter 30 and can be removed from the patient. Device 11 remains deployed in the patient, and retains a valve function in the bodily passageway. In the illustrated device 11, this valve function is retained in the absence of any remaining stent component, i.e. providing an implanted, stentless valve.

Figure 5:
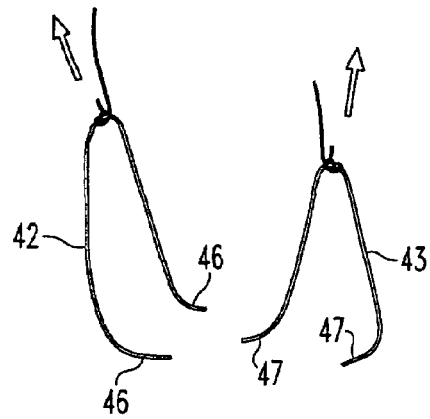
FIG. 5 provides a perspective view of removable frame elements from the device of FIG. 4.
Figure 6:
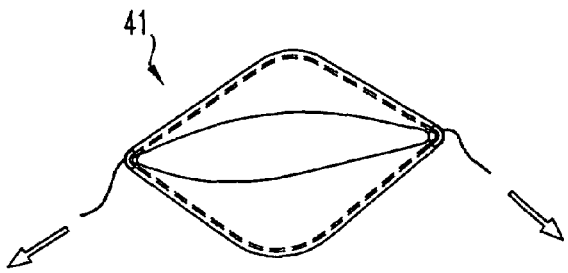
FIG. 6 provides a top view of the device of FIG. 4.

With reference now to FIGS. 4 through 7, shown is another valve device 41 of the present invention. Device 41 generally includes features similar to those of device 11, except as described otherwise herein. Device 41 includes frame elements 42 and 43 of differing configuration than those of device 11. In particular, frame elements 42 and 43 are adapted for removal from device 41 in a direction opposite that of device 11. In this regard, frame elements 42 and 43 are removed in a direction corresponding to that of blood flow (see arrow, FIG. 4) as opposed to frame elements 13 and 14 which were designed for removal in a direction opposite that of blood flow (see arrow, FIG. 1). In this design, frame elements 42 and 43 traverse the lateral edges of one side of each of the legs 44 and 45 of the device 41. Referring particularly to the cutaway portion in FIG. 4, the frame elements 42 and 43 are configured to curve to sections that bend partially around the arcuate terminus of legs 44 and 45 but not so far around that removal of the frame elements 42 and 43 would be prevented. These curved sections 46 and 47 are thus able to pass through sleeves 48 and 49 without substantial damage thereto, and in this regard may be configured to have a suitable level of stiffness to deform from the illustrated curved configuration to a straight configuration during removal. With reference to FIG. 5 and FIG. 6, illustrated by the arrows is the direction of removal of frame elements 42 and 43 (see arrows).

Figure 7A:
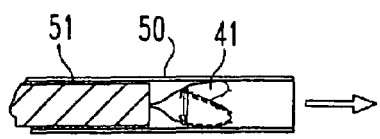
FIG. 7A through 7C provide illustrations of a deployment of the valve device of FIG. 4.
Figure 7B:
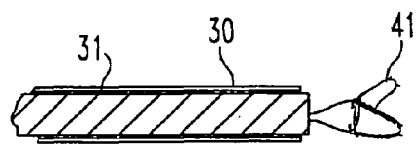
Figure 7C:
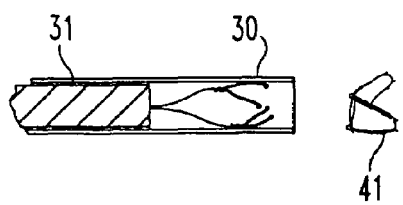

FIGS. 7A through 7C illustrate the deployment of device 41 within a bodily passage. FIG. 7A shows the device 41 in its compressed or contracted configuration residing within the lumen of a delivery device such as a catheter 50. Push rod 51 is used deploy the device 41 in the direction of the arrow, whereupon it assumes its expanded configuration as shown in 7B. Retraction of the push rod 51 then pulls frame elements 42 and 43 back into catheter 50 for removal from the patient.

Figure 2A:
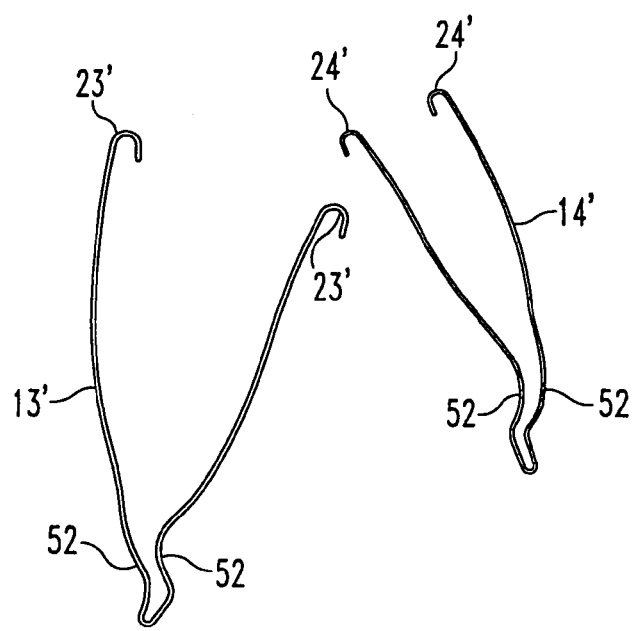
FIG. 2A provides a perspective view of modified removable frame elements.

It will be understood that devices 11 and 41 could also be modified to reside for a period of time while retaining their associated frame elements, and the frame elements later removed, e.g. after a period of tissue growth and attachment of wall-contacting portions of devices 11 and 41 to the walls of the bodily passage. In this regard, the frame elements would not be connected to the pusher rod or other device used for deployment; rather, the frame elements would be later retrieved with a catheter-deployed retrieval device such as a snare or basket. For such purposes, the frame elements can optionally be modified to have portions extending inwardly from the walls of the bodily passage upon deployment, to facilitate connection to and removal of the frame elements. Illustratively, FIG. 2A depicts frame elements 13' and 14' having features similar to those of frame elements 13 and 14 shown in FIG. 2, except also including bends 52. Frame elements 13' and 14' can be incorporated with the other elements of device 11 to provide a modified version thereof. Bends 52 are configured such that upon deployment of such a modified valve device, the connection adaptations 20 and 21 are positioned residing inward of and away from the vessel walls, to facilitate ready connection to and retrieval of the associated frame elements. Similar modifications could also be made to frame elements 42 and 43 of device 41 depicted in FIGS. 4-7.

Figure 8:
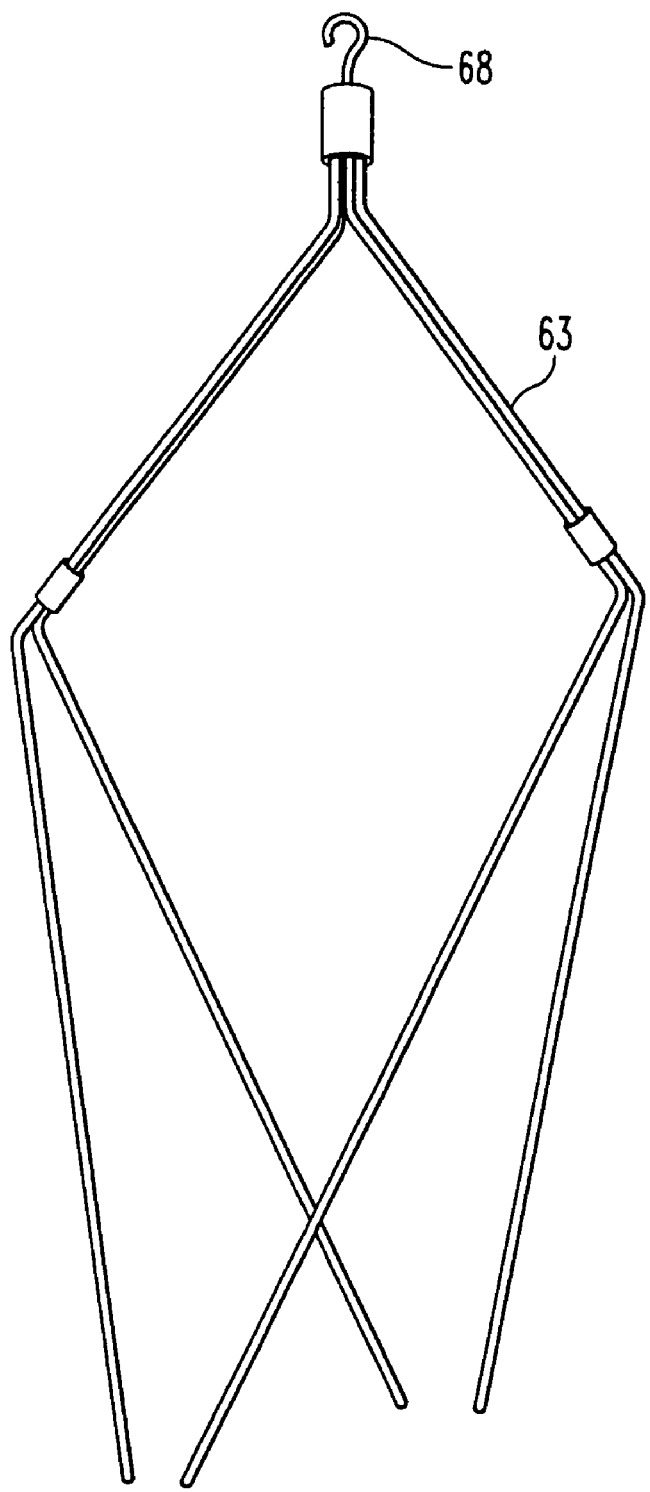
FIG. 8 provides a perspective view of a frame element of the invention.
Figure 9:
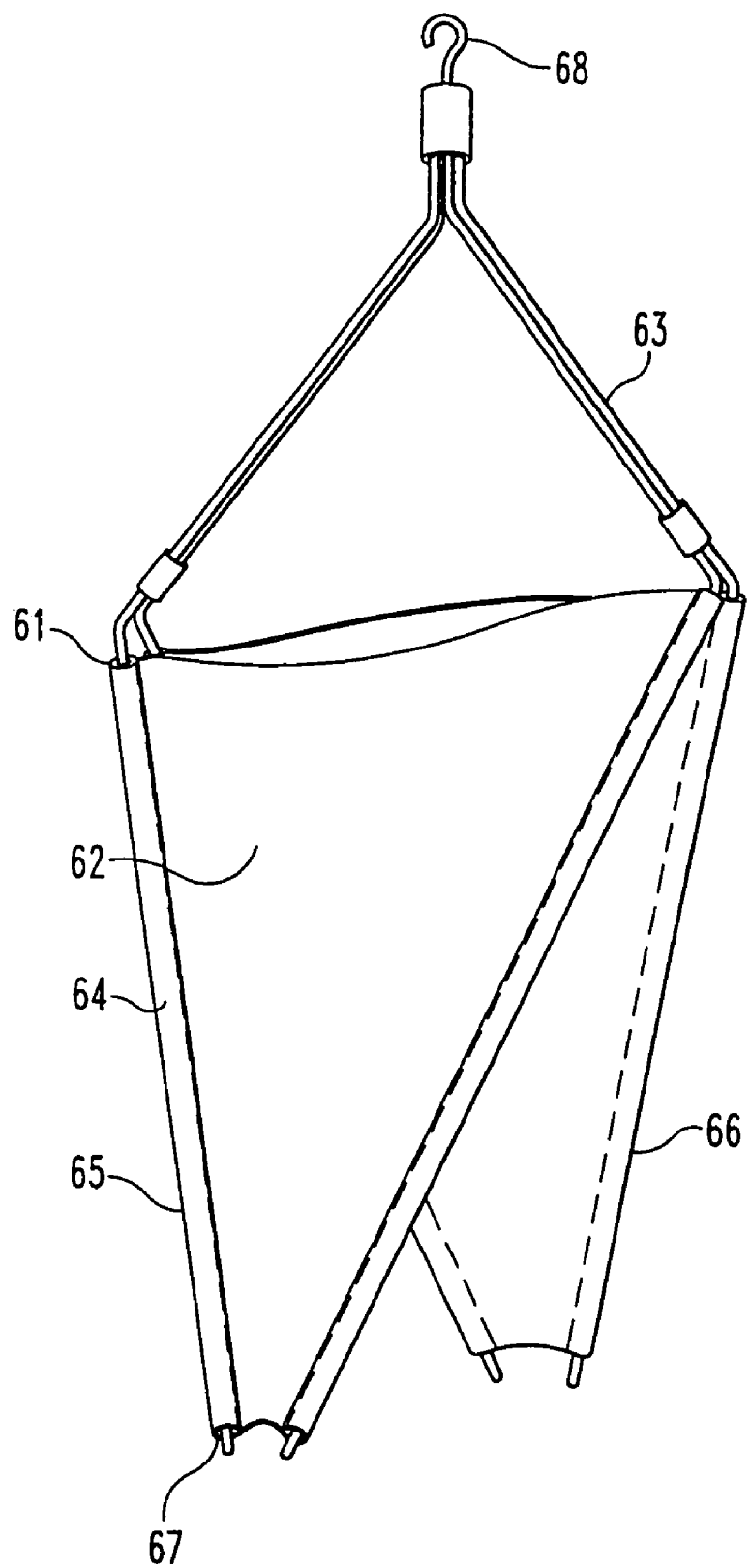
FIG. 9 provides a perspective view of an alternative valve device of the invention.

With reference to FIGS. 8 through 12, shown is a valve device with a single frame element. Specifically, FIG. 8 illustrates a frame element 63 of the present invention. Frame element 63 is similar to frame elements 42 and 43 of device 41 inasmuch as frame element 63 is designed for removal from its respective device in a direction opposite to that of blood flow. Frame element 63 differs from frame elements 42 and 43 inasmuch as frame elements 42 and 43 are configured to curve to sections that bend partially around the arcuate terminus of legs 44 and 45 of device 41 but not so far around that removal of the frame elements 42 and 43 would be prevented. Frame element 63, however, is configured such that the ends of frame element 63 are substantially straight and extend through legs 65 and 66 of device 61. Valve device 61 also differs from device 41 in that there are four sleeves present in valve device 61, rather than two. Moreover, flexible material 62 of device 61 is different from the flexible material present in devices 11 and 41 in that flexible material 62 is triangular in shape, rather than rounded at the bottom. Taken together, these adaptations allow for frame element 63 to extend through the open end 67 of each sleeve 64 (see FIGS. 9 and 10).

Figure 10:
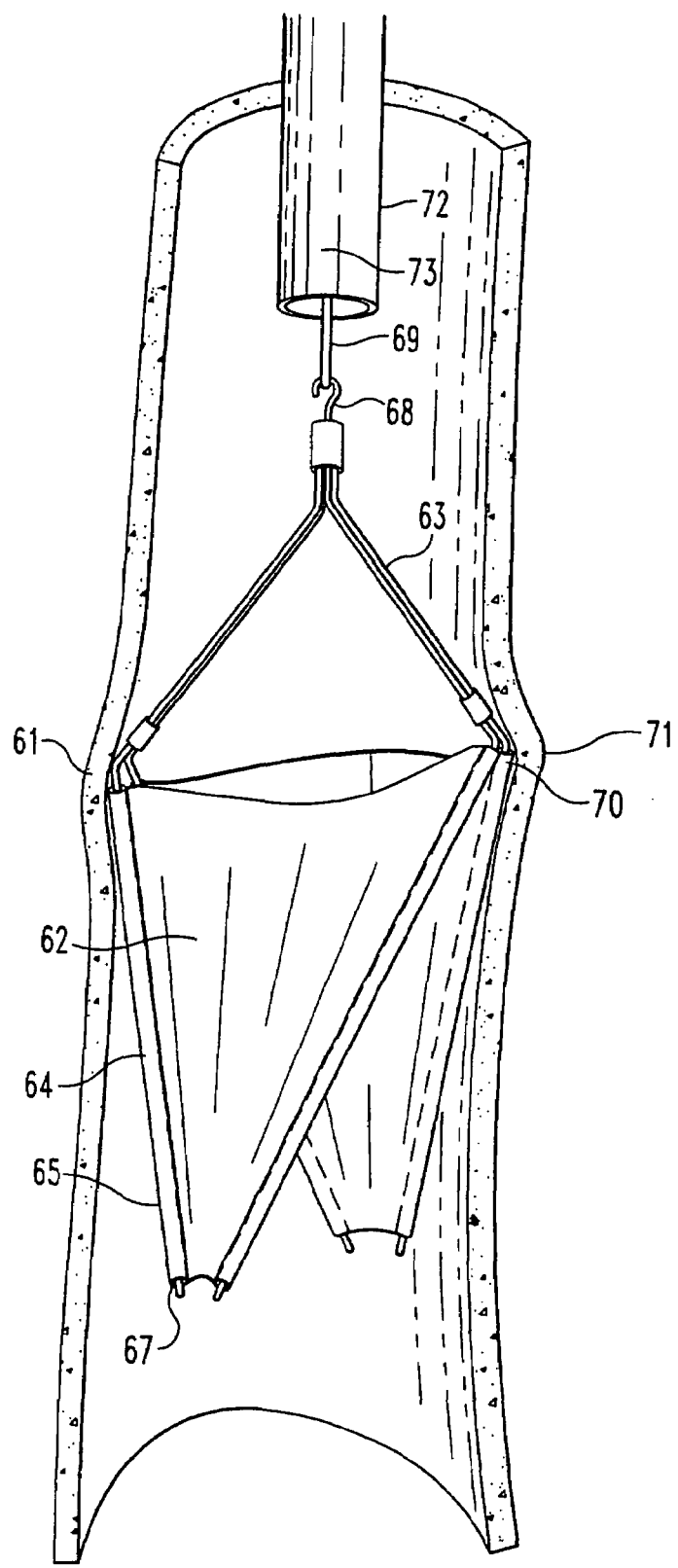
FIG. 10 provides a perspective view of the deployment of the valve device depicted in FIG. 9, wherein the edges of the valve have become attached to the walls of a vascular passage.
Figure 11:
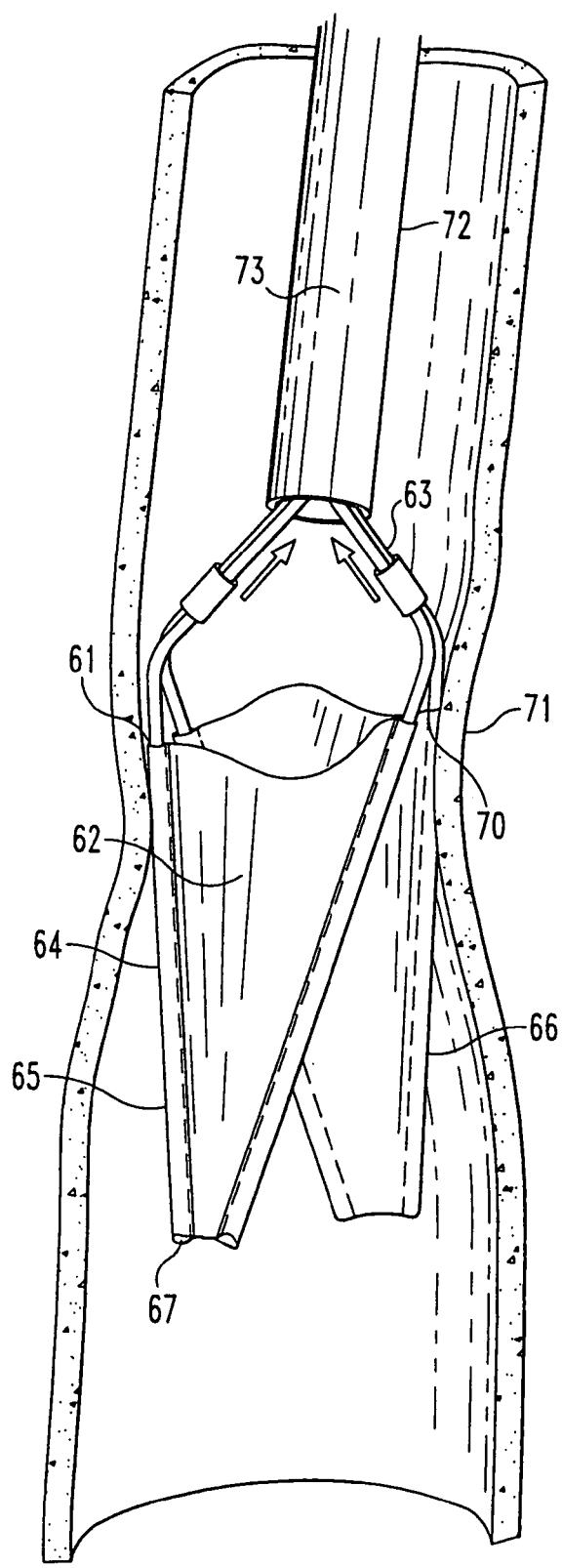
FIG. 11 provides a perspective view of the valve device depicted in FIG. 10, wherein the frame element has been partially removed from the valve device.
Figure 12:
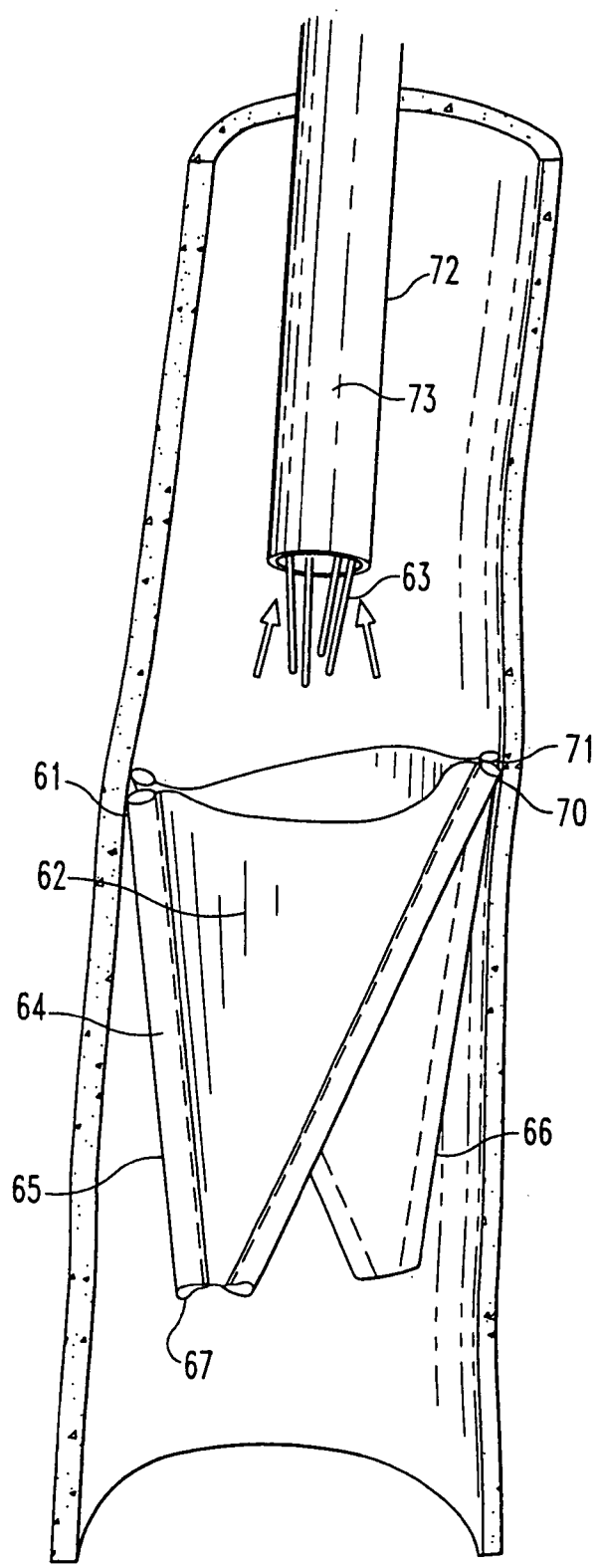
FIG. 12 provides a perspective view of the valve device depicted in FIG. 10, wherein the frame element has been completely removed from the valve device.

FIGS. 10 through 12 illustrate the deployment and removal of frame element 63 from valve device 61. Push rod 73 is used to first deploy device 61 into a bodily passage. Push rod 73 contains an eyehook 69, which connects to hook 68 of frame element 63 to allow for deployment of device 61 into a bodily passage. After the device has been deployed to a desired location, the frame element 63 can be immediately removed if desired. Alternatively, prior to removal of the frame element 63, tissue ingrowth can be allowed to occur into the edges 70 of device, and potentially other areas of the device, to attach the device to the walls 71 of the bodily passage with tissue. Once sufficiently attached by tissue ingrowth, which in certain embodiments may take several days, e.g. at least about 3 days and sometimes in the range of about 5 to 7 days or more, frame element 63 can be removed from device 61. Retraction of push rod 73 pulls frame element 63 back into catheter 72 for removal from the patient (see FIGS. 11 and 12).

Figure 13:
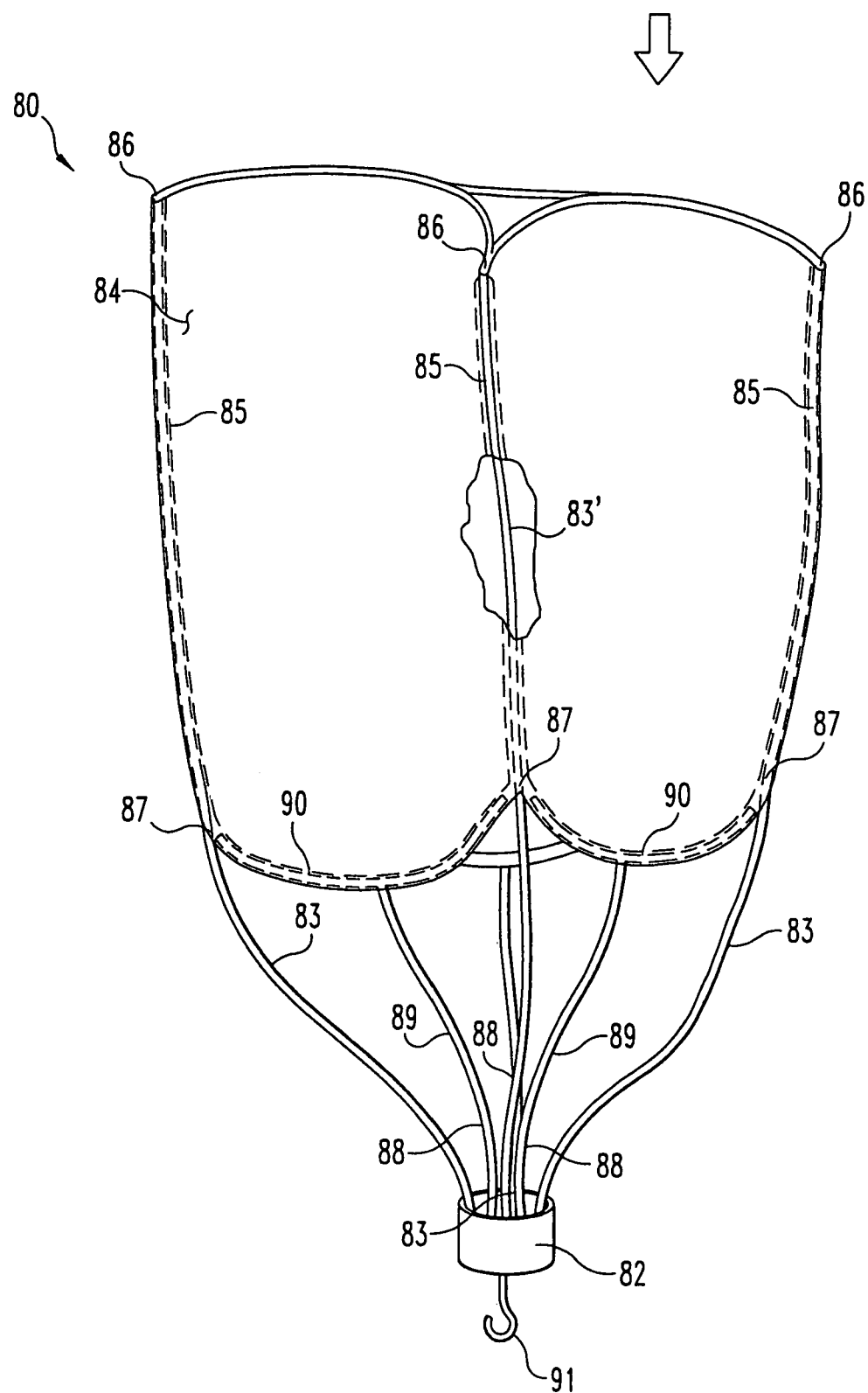
FIG. 13 provides a perspective view of another valve device of the invention.
Figure 14:
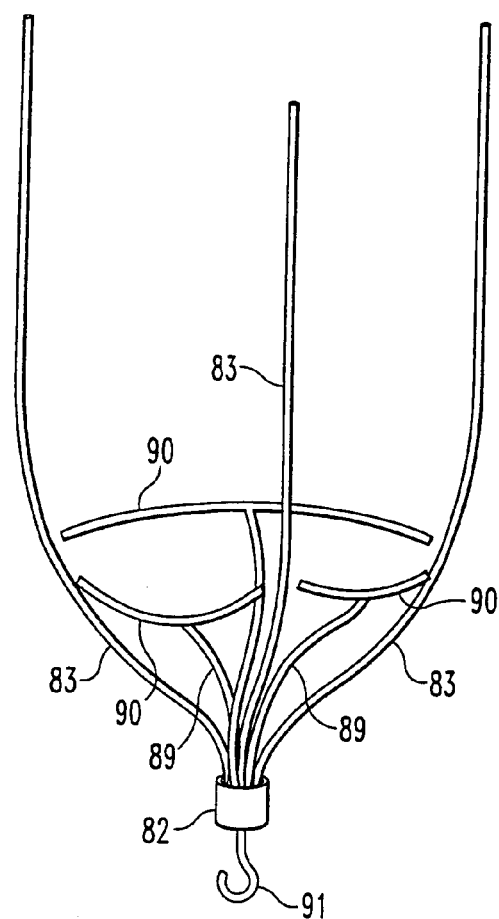
FIG. 14 provides a perspective view of the frame incorporated into the valve device of FIG. 13.
Figure 15:
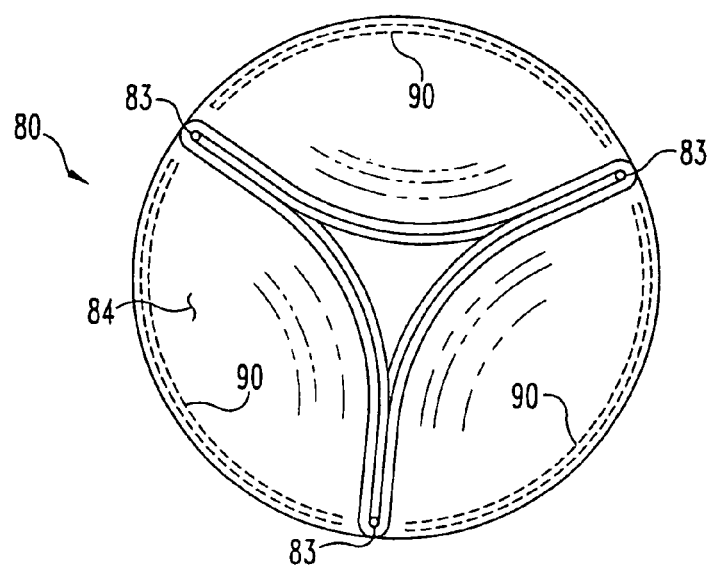
FIG. 15 provides a top view of the valve device of FIG. 13 in a closed condition.

With reference to FIGS. 13-15, depicted is another valve device of the present invention, constructed with a wire frame somewhat similar to that found in percutaneous filter devices. In particular, valve device 80 includes a frame 81 including a central element 82 and a plurality of attached wires 83 extending therefrom. Wires 83 diverge outwardly from the central element 82 and provide elongate segments that, when deployed, are forced against the lumen of a vascular vessel such as a vein or artery. A flexible material 84 is carried on the frame 81, and is configured to provide a plurality of leaflets for the valve 80. Although the illustrated device has three leaflets, it will be understood that similar devices could have two, three, four, five or more leaflets. In the depicted device, the wires 83 are received within elongate pockets 85 or sleeves of the flexible material 84, as illustrated at position 83' shown in a cutaway portion of pocket 85. Pockets 85 can be fashioned in any suitable manner, including for example by suturing or sewing. As well, pockets 85 can be formed from the same material as the remainder of the flexible material 84, or all or in part of a different material attached to the remainder of the flexible material 84. Pockets 85 in the illustrated device each have a closed upper end 86 and an open lower end 87 for receiving the wires 83.

Frame 81 in the illustrated device 80 also includes a second set of wire elements 88 providing retaining struts adapted to force and retain lower edges of flexible material 84 against the lumen wall to create partial or essentially complete seal against the lumen wall. Wire elements 88 can include a first portion 89 connected to central element 82 and a second, arcuate transverse arm 90 connected to first portion 89. First portion 89 is configured to radially force transverse arm 90 against the lumen wall to create the partial or essentially complete seal as discussed, sufficient for valve function. In this regard, it will be understood that instead of having transverse arm 90, a plurality of additional wire portions 89 could be provided with each wire portion having an end positioned inside of and forcing the flexible material against the lumen wall, to provide a sufficient seal for valve function.

Frame 81 of device 80 also includes a retrieval element such as a hook 91, connected to central element 82. Frame 81 in device 80 is desirably self-expanding, and is collapsible for delivery through the lumen of a delivery device such as a catheter or sheath. Such a device 80, in use, can be deployed from the lumen of the delivery device, whereupon it will expand within the vascular lumen. Wires 83 will force the flexible material 84 against the lumen wall generally in a longitudinal band relative to the axis of the lumen, although this may be varied to encompass both longitudinal and circumferential directions by varying the design of wire elements 83. On the other hand, the segments of flexible material 84 spanning between wires 83 will be free to collapse inwardly in response to blood flow in the direction of the arrow, FIG. 13. The resulting valving function will be facilitated by transverse arms 90, which force a band at or near the lower edge of the flexible material 84 against the lumen wall and restrict blood leakage around the outside of device 80.

After the flexible material 84 has been attached via tissue growth to the lumen wall, frame 81 can be removed. For example, where flexible material 84 is a remodelable material, device 80 can be left implanted with frame 81 for several days or longer, sufficient to significantly remodel material 84 and attach material 84 to the lumen wall generally in areas forced against the lumen wall by wires 83 and transverse arms 90. Then, using standard percutaneous retrieval techniques, frame 81 can be grasped by hook 91, retrieved into the lumen of a catheter or other retrieval device, and removed from the patient. In this manner, a functioning, frameless valve can be provided in the patient.

Figure 13A:
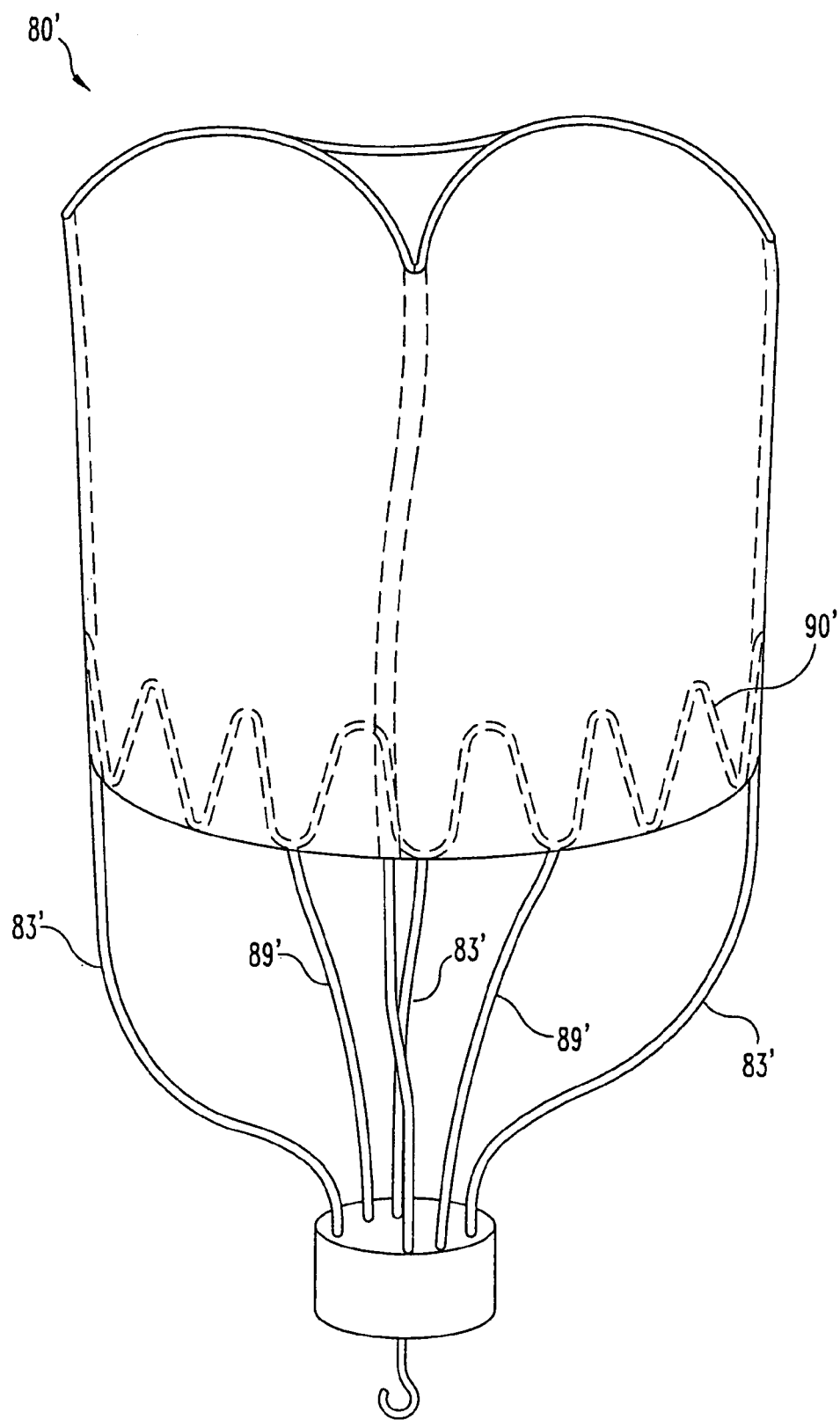
FIG. 13A provides a perspective view of another valve device of the invention.

In a modification of valve device 80, 20 transverse arms 90 can be connected to one another on each end, or integrally formed as a single, annular element. Upon retrieval of the wires portions 89 into a catheter or sheath, the annular element would be radially collapsed for receipt into the catheter or sheath. Similarly, depicted in FIG. 13A is a modified valve device 80' similar to device 80 of FIG. 13, except instead of having transverse arms 90, the removable frame includes an annular serpentine stent 90' such as a Gianturco Z-type stent, which compresses lower portions of the flexible material 84 against the lumen wall. Again, upon retrieval of the frame 81 with wire portions 89' into a catheter or sheath for removal from the patient, the stent 90' would be caused to radially collapse for receipt within the lumen of the catheter or sheath.

Figure 16:
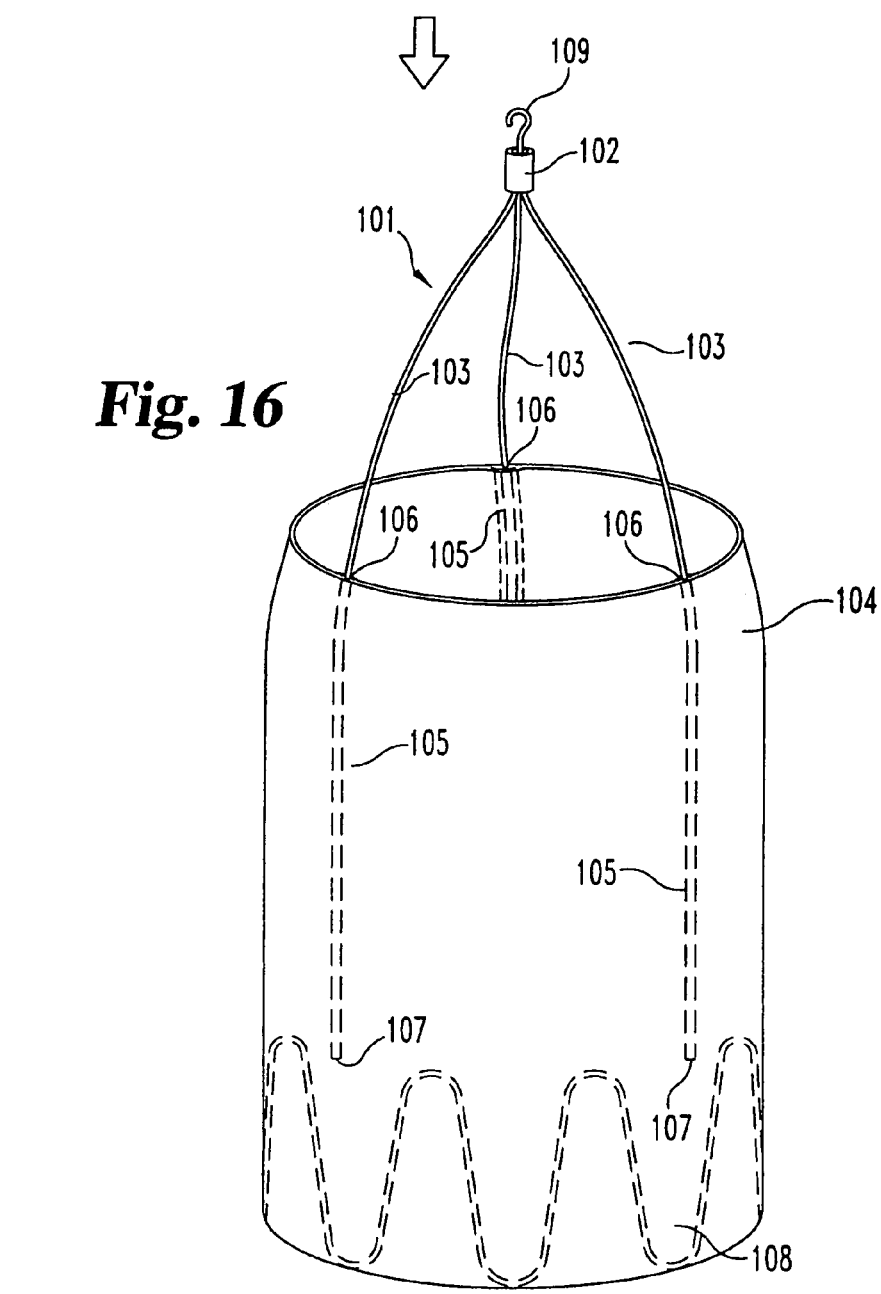
FIG. 16 provides a perspective view of another valve device of the invention.
Figure 17:
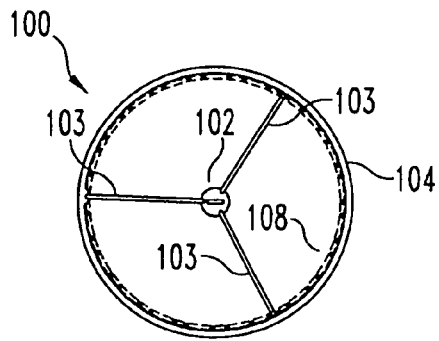
FIG. 17 provides a top view of the valve device of FIG. 16 in an open condition.
Figure 18:
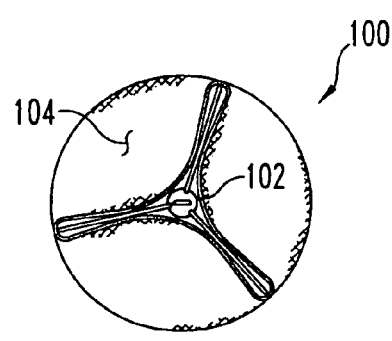
FIG. 18 provides a top view of the valve device of FIG. 16 in a closed condition.

With reference now to FIGS. 16-18, shown is another medical valve device 100 of the invention, configured for removal of only a portion of the original frame. Valve device 100 includes a wire frame 101 somewhat similar to a percutaneous filter, as in device 80 discussed above. Frame 101 thus includes central element 102 and a plurality of wires 103 connected to central element 102 and diverging outwardly therefrom. Wires 103 thereby provide longitudinally-extending segments that are forced against the lumen walls of a vascular or other vessel into which device 100 is inserted. Device 100 also includes flexible material 104, and wires 103 may be received within sleeves or pockets 105 of or attached to flexible material 104, such that wires 103 force adjacent areas of flexible material 104 against the lumen wall. Pockets 105 may have an open upper end 106, and a closed lower end 107. Alternatively, both ends may be open.

Valve device 100 also includes an annular frame member 108, for example a stent (e.g. a Gianturco Z-stent type having a generally serpentine wire element as shown), connected to the flexible material 104. Frame member 108 in device 100 is configured to force a band of adjacent flexible material 104 sufficiently against the lumen wall to create a seal effective for the valving function of the valve device 100. In this regard, frame member 108 can be positioned on the inside or outside of flexible material 104, or received within a pocket formed in flexible material 104. Desirably, frame member 108 is received on the inside of flexible material 104. In the illustrated embodiment, connection between the frame member 108 and the flexible material 104 can be achieved by any suitable means, including for example suturing, bonding, crosslinking using chemical agents or radiation, welding, and the like.

In use, device 100, in self-expanding form, can be collapsed and loaded into a delivery device such as a catheter or sheath. Upon deployment from the delivery device, e.g. using a push rod or other mechanism, wires 103 will expand radially, and frame 108 will expand radially, thus anchoring the device 100 against the lumen wall. Flexible material 104 occurring between wires 103 will collapse and expand to provide valve function, as illustrated in the top views of FIGS. 17 (open condition) and 18 (closed condition). In this regard, to facilitate the inward collapse of the leaflets in response to liquid flow in the direction of the arrow (FIG. 16), the upper edge of the flexible material 104 as deployed may be carried slightly inward from the lumen wall by the wire elements 103, as illustrated. This will assist in ensuring the impingement of fluid flowing in the direction of the arrow upon outer surfaces of the flexible material and the consequent inward collapse of the flexible material to close the valve orifice. Conversely, flow in the opposite direction will force the flexible material out towards the walls of the lumen, opening the valve orifice.

Device 100 can be left implanted with frame 101 in place for a period of time sufficient to achieve tissue growth and selective attachment of areas of flexible material 104 to the lumen wall. This selective attachment will occur at least along bands of flexible material forced against the lumen wall by wires 103, and optionally also by frame 108. Remodelable flexible materials will be preferred for these purposes. After such attachment, the frame 101 can be retrieved into a catheter or other retrieval device using hook 109 or another suitable retrieval piece, leaving in place a functional valve including the flexible material 104 and the frame 108. In addition, frame 108 may be constructed of a biodegradable or non-biodegradable material. When constructed of a biodegradable material, upon biodegradation of frame 108, a functional, frameless valve will be provided within the patient.

In an alternative embodiment, the ends of wires 103 can be connected to the annular frame 108 (including for example integrally formed therewith), and the entire frame assembly including frame 101 and annular frame 108 can be received on the inside of the flexible material 104, e.g. with the flexible material in the form of a tube. After a suitable implant and growth period for tissue attachment, generally as discussed above, the frame assembly 101/108 can be retrieved, leaving in place a functional, frameless valve. For these purposes, a remodelable flexible material will be preferred.

In a further alternative embodiment, the ends of wires 103 can be releasably connected to the annular frame 108, and the entire frame assembly including frame 101 and annular frame 108 can be received on the inside of the flexible material 104, e.g. with the flexible material in the form of a tube. The releasable connection may be achieved, for example, by a biodegradable material in the form of a suture or other connector, receipt of ends of wires 103 within female connectors, or the like. After a suitable implant and growth period for tissue attachment, and for degradation of any biodegradable material used to connect wires 103 and frame 108, the frame assembly 101 can be retrieved, leaving in place a functional valve including flexible material 104 and frame 108. For these purposes, a remodelable flexible material will be preferred.

It will be understood that in each of the embodiments illustrated and described in conjunction with FIGS. 1-18, additional, temporary attachments between the flexible material and one or more of the frame components may be included in the device as deployed, to stabilize aspects of the device upon initial implant and until tissue growth and attachment can occur. For example, a biodegradable suture or adhesive material may be used to attach the flexible material to the frame elements, wherein the biodegradable material substantially or completely degrades after implantation and prior to removal of the frame elements. Illustratively, such sutures, adhesives or other biodegradable materials could be used to attach portions of frame elements 13,14 (FIGS. 1-3), 42,43 (FIGS. 4-6), 63 (FIGS. 8-12), 83 and/or 90 or 90' (FIGS. 13-15), and 103 and/or 108 (FIGS. 16-18) to the flexible material, instead of or in addition to the use of any pockets or sleeves as described above.

It will also be understood that in each of the embodiments illustrated in FIGS. 1-18, suitable imagable (e.g. radiopaque) materials can be incorporated into the frame elements and/or flexible materials. Illustratively, radiopaque materials such as gold or other imagable materials can be incorporated onto, into or as frame elements which will be snared or otherwise connected in a frame retrieval operation. This may include for example the hooks, loops or eyelets incorporated for these purposes as well as adjacent elements such as central elements 82 and 102 depicted in FIGS. 13-18.

The flexible material (e.g., 12, FIG. 1) used in the invention is a biocompatible material, and is preferably a remodelable material. Suitable remodelable materials may be made from natural or synthetic polymers, and preferred materials comprise collagen. Thus, in general, the flexible material may comprise a material such as synthetic biocompatible polymers such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof; polylactic acid, polyglycolic acid or copolymers thereof, a polyanhydride, polycaprolactone, polyhydroxybutyrate valerate, polyhydroxyalkanoate, or another biodegradable polymer.

In certain embodiments of the invention, the flexible material 12 is comprised of a naturally-derived or synthetic collagenous material, and especially an extracellular matrix material. Suitable extracellular matrix materials include, for instance, submucosa (including for example small intestinal submucosa, stomach submucosa, urinary bladder submucosa, or uterine submucosa), renal capsule membrane, dura mater, pericardium, serosa, peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present invention, and their isolation and treatment, reference can be made to U.S. Pat. Nos. 4,902,508, 5,554,389, 5,993,844, 6,206,931, and 6,099,567. Renal capsule tissue can also be obtained from warm blooded vertebrates, as described more particularly in copending U.S. patent application Ser. No. 10/186,150 filed Jun. 28, 2002 and International Patent Application serial No. PCT/US02/20499 filed Jun. 28, 2002, published Jan. 9, 2003 as W003002165.

Frame elements of the present invention may also be configured from any suitable biocompatible material. These include for example metals such as Nitinol or other shape-memory materials, or stainless steel, as well as resorbable or nonresorbable polymeric materials. Similar materials may also be used to form barbs in devices of the invention.

Any suitable means can be used to remove a frame element from a valve device. Suitable means include, for example, deploying a push rod having an eye hook through a catheter and connecting the eye hook to a hook present on a frame element. The push rod can then be retracted up into or through the catheter, thereby effectively removing the frame element from the valve device. Alternatively, the frame element can be constructed with an eye hook, or similar structure, and the push rod be constructed with a hook. While hooks and eye hooks are a preferred embodiment of the present invention, it will be understood that the push rod and frame element can be constructed in any suitable manner, which provides for efficient deployment and removal. As well, standard percutaneous retrieval devices such as snares or baskets may be used to retrieve frame elements, after a period of implantation. Accordingly, the adaptations identified herein should not be construed in any way as limiting deployment and removal means.

In instances where the frame element is removed after the device has become attached to the walls of a bodily passage, the remodelable valve material can if desired be modified such that the frame element can be removed earlier. For example, perforations, roughened fringe, or other surface modifications can be provided at the edge of the valve material such that attachment is enhanced.

The frame element or elements also may be coated with a composition to help prevent the permanent attachment of the removable frame element(s) to the flexible material and/or to the walls of a bodily passage. This allows for a frame element to be removed without damaging the valve device or the bodily passage where it is being retracted. Any suitable composition can be applied to the frame element. Suitable compositions include, for example, antiproliferative agents, including for example paclitaxel and other taxol derivatives, for instance as identified in U.S. Pat. Nos. 5,157,049 and 5,616,608, rapamycin, or polymeric coatings, e.g. polytetrafluoroethylene (PTFE) or lubricous hydrophilic coatings, these also potentially containing and releasing other agents such as antiproliferative agents.

Devices of the invention are desirably adapted for deployment within the vascular system, and in particularly preferred embodiments, devices of the invention are adapted for deployment within the venous system. Accordingly, preferred devices such as devices 11 and 41 are adapted as venous valves, for example for percutaneous implantation within veins of the legs or feet, to treat venous insufficiency.

It will be understood that other valve devices having one or more removable frame elements are contemplated as being within the scope of the present invention. For example, the valves disclosed in published U.S. patent application Ser. No. 777,091 filed Feb. 5, 2001, published as 20010039450 on Nov. 8, 2001, can be modified to have one or more removable frame elements, for example to provide stentless valve grafts remaining in the vessel or other similar body passageway, and such devices are contemplated to be within the scope of the present invention. As well, aspects of the present invention can also be extended to other medical devices configured for implantation within bodily passages, especially the vascular system. For example, removable frame elements can be incorporated into other vascular devices incorporating flexible materials, e.g. other devices having flexible portions extending into the vascular lumen such as occluder devices which completely block the lumen. Such devices wherein the flexible material is remodelable will be of particular advantage in the present invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are indicative of the abilities of those of ordinary skill in the art and are hereby incorporated by reference in their entirety as if individually incorporated by reference and fully set forth.

What is claimed is:

1. A vascular valve device, comprising:
an artificial valve for deployment within a vascular passage, the artificial valve including flexible material and at least two frame elements;
said frame elements adapted for removal after deployment of said artificial valve in the vessel; and
said artificial valve device configured to provide a valve function after removal of said frame elements.

2. The device of claim 1, wherein the frame elements are attached to one another during deployment of the artificial valve device.

3. The device of claim 1, wherein the frame elements are unattached to one another during deployment of the artificial valve device.

4. The device of claim 1, wherein said frame elements each include a member extending longitudinally along and circumferentially around the vascular passage after deployment and before removal.

5. The device of claim 1, wherein said artificial valve device comprises barbs for attaching to a wall of the vessel.

6. The device of claim 1, wherein the flexible material is a remodelable material.

7. The device of claim 1, wherein the flexible material is collagenous.

8. The device of claim 1, wherein the flexible material comprises an extracellular matrix material.

9. A vascular valve device, comprising:
an artificial valve for deployment within a vascular passage, the artificial valve including flexible material and at least one frame element coated with an antiproliferative composition;
said frame element adapted for removal after deployment of said artificial valve in the vessel; and
said artificial valve device configured to provide a valve function after removal of said frame element.

10. The device of claim 9, wherein the composition comprises paclitaxel.

11. A vascular valve device, comprising:
an artificial valve for deployment within a vascular passage, the artificial valve including flexible material, at least one removable frame element and at least one non-removable frame element;
said removable frame element adapted for removal after deployment of said artificial valve in the vessel; and
said artificial valve device configured to provide a valve function after removal of said removable frame element.

12. The device of claim 11, wherein said non-removable frame element is biodegradable.

13. A vascular valve device, comprising:
an artificial valve for deployment within a vascular passage, the artificial valve including flexible material and at least one frame element;
said frame element adapted for removal after deployment of said artificial valve in the vessel, wherein said at least one frame element comprises a retrieval element adapted to reside away from a wall of said passage upon deployment of said device in said passage; and
said artificial valve device configured to provide a valve function after removal of said frame element.

14. The device of claim 13, wherein said retrieval element comprises a hook or loop.

15. A method for providing a valve device in a vascular passage, comprising:
deploying within said passage an artificial valve device including a flexible material and at least two frame elements removable after said deploying; and
removing said frame elements so as to leave said artificial valve device within said vascular passage absent said frame elements, wherein said removing includes removing each of said frame elements.

16. The method of claim 15, wherein the at least two frame elements comprise an antiproliferative composition.

17. The method of claim 16, wherein the composition comprises paclitaxel.

18. The method of claim 15, wherein the at least two frame elements are removed after the artificial vascular device has become attached to the vascular passage.

19. The method of claim 15, wherein said flexible material is a remodelable material.

20. The method of claim 19, wherein said remodelable material is collagenous.

21. The method of claim 20, wherein said collagenous remodelable material is an extracellular matrix material.

* * * * *